US005773548A

United States Patent [19]

Schickmann et al.

[11] Patent Number: 5,773,548

[45] Date of Patent: Jun. 30, 1998

[54] CATALYST FOR PREPARING ORGANOSILOXANES OR POLYORGANOSILOXANES

[75] Inventors: Harald Schickmann, Meissen; Robert Lehnert, Dresden; Heinz-Dieter Wendt, Radebeul; Holger Rautschek, Nuenchritz; Harald Roesler, Dresden; Hans-Guenther Srebny, Duelman, all of Germany

[73] Assignee: Huels Silicone GmbH, Nuenchritz, Germany

[21] Appl. No.: 569,139

[22] PCT Filed: Jun. 22, 1994

[86] PCT No.: PCT/EP94/02032

§ 371 Date: Jan. 11, 1996

§ 102(e) Date: Jan. 11, 1996

[87] PCT Pub. No.: WO95/01983

PCT Pub. Date: Jan. 19, 1995

[30] Foreign Application Priority Data

| | | | |
|---|---|---|---|
| Jul. 10, 1993 | [DE] | Germany | 43 23 183.7 |
| Jul. 10, 1993 | [DE] | Germany | 43 23 184.5 |
| Jul. 10, 1993 | [DE] | Germany | 43 23 185.3 |
| Dec. 27, 1993 | [DE] | Germany | 43 44 664.7 |

[51] Int. Cl.[6] .................................................... C08G 77/06

[52] U.S. Cl. ........................... 528/18; 502/150; 502/158; 502/159; 502/162; 528/28; 528/23

[58] Field of Search .................................... 502/150, 158, 502/159, 162; 528/28, 18, 23

[56] References Cited

U.S. PATENT DOCUMENTS

| | | | |
|---|---|---|---|
| 3,652,711 | 3/1972 | Triem et al. | 260/825 |
| 3,839,388 | 10/1974 | Nitzche et al. | 260/448.2 E |
| 5,099,051 | 3/1992 | Beck et al. | 528/23 |
| 5,210,131 | 5/1993 | Gilson et al. | 528/23 |
| 5,420,221 | 5/1995 | Razzano et al. | 528/18 |
| 5,534,608 | 7/1996 | Thomposon et al. | 528/23 |

*Primary Examiner*—Glenn Caldarola
*Assistant Examiner*—Nadine Preisch
*Attorney, Agent, or Firm*—Oblon, Spivak, McClelland, Maier & Neustadt, P.C.

[57] ABSTRACT

The invention relates to a catalyst for preparing organosiloxanes and polyorganosiloxanes which are obtained primarily by polycondensation processes. The catalyst of the invention is a reaction product of phosphonitrilic chloride with a compound of the general formula $[R_3SiO(R_2SiO)_m]_3P{=}O$ (I), where R are, independently of one another, identical or different, unsaturated and/or saturated monovalent hydrocarbon radicals having from 1 to 6 carbon atoms or hydrogen, with the proviso that only one hydrogen atom is bound to each silicon atom and m has a value between 0 and 1000. Volatile chlorine-containing silicon compounds formed during the reaction can, if required, be completely or partially removed.

13 Claims, No Drawings

CATALYST FOR PREPARING ORGANOSILOXANES OR POLYORGANOSILOXANES

TECHNICAL FIELD

The invention relates to a catalyst for preparing organosiloxanes or polyorganosiloxanes which are obtained primarily by polycondensation processes. The catalyst of the invention is a reaction product of phosphonitrilic chloride with a compound of the general formula $[R_3SiO(R_2SiO)_m]_3P{=}O$ (I), where R are, independently of one another, identical or different, unsaturated and/or saturated monovalent hydrocarbon radicals having from 1 to 6 carbon atoms or hydrogen, with the proviso that only one hydrogen atom is bound to each silicon atom and m has a value between 0 and 1000. Volatile chlorine-containing silicon compounds formed during the reaction can, if required, be completely or partially removed. Organosiloxanes and polyorganosiloxanes are important intermediates and final products of silicon chemistry.

PRIOR ART

For the preparation of organosiloxanes and polyorganosiloxanes, two different basic chemical processes are essentially known for industrial applications.

One process is the ring-opening polymerization of cyclic polysiloxanes, combined with the incorporation of mono-, di- and/or trifunctional silicon compounds, also known as equilibration. However, this reaction proceeds only to a chemical equilibrium at which about 87% by weight of linear polysiloxanes and about 13% by weight of cyclosiloxanes are present. These have to be separated in a subsequent process step.

In the second process, the starting materials are low-molecular-weight (oligomeric) siloxanes containing OH groups, and these are subjected to a polycondensation reaction. Here too, the incorporation of mono-, di- and/or trifunctional silicon compounds is possible. Attempts are made to counteract the formation of cyclic siloxanes by means of suitable catalysts, so as to avoid additional removal of the cyclic compounds.

For both process methods, use is customarily made of basic or acid catalysts. Known basic catalysts are, inter alia, potassium hydroxide, potassium siloxanolates or ammonium and phosphonium siloxanolates. The group of acid catalysts includes, for example, sulphuric acid, trifluoromethanesulphonic acid, acid ion exchange resins, acid-activated Fuller's earths and phosphonitrilic chlorides.

Most catalysts which are of importance for polycondensation reactions of silanols and siloxanols also cause a more or less rapid equilibration reaction, which results in the formation of cyclic siloxanes.

Owing to their high activity in addition to a good selectivity, almost no equilibration takes place, phosphonitrilic chlorides are very suitable as catalysts for polycondensation reactions of silanols and siloxanols.

Phosphonitrilic chlorides and compositions containing them are known (Nitzsche et al. DE-B 12 79 019, Nitzsche et al. U.S. Pat. No. 3,839,388). Solvents which are proposed are, for example, benzene, toluene, petroleum ether, halogenated hydrocarbons, ethers and ketones (Triem et al. U.S. Pat. No. 3,652,711).

However, phosphonitrilic chlorides are only very slightly soluble in non-polar solvents such as, for example, aliphatic and aromatic hydrocarbons. This has the disadvantage that the phosphonitrilic chlorides are, owing to their very low concentration in the solutions, particularly susceptible to impurities or to hydrolysis. For this reason, such solutions often have only a low storage stability, and the activity of the catalyst drops quickly.

Solvents such as ethers, ketones and esters are not completely inert to the phosphonitrilic chlorides, which likewise leads to deactivation of the catalyst with the entire solution becoming dark in colour.

A further variant for preparing phosphonitrilic chloride solutions is the addition of surfactants or crown ethers as solubilizers, for example ethyl acetate (Schuster, J. et al. EP 381 204). This makes the preparation of the catalyst solution a complicated, multistage process. In the subsequent preparation of the polyorganosiloxanes, the surfactants or crown ethers used remain in the product and can interfere in the further processing of the polymer. In addition, long storage of the catalyst solution results in ester cleavage and thus in decomposition of the solvent.

As a result, in most cases, a solution of the phosphonitrilic chloride in an organic solvent has the obstacle of either the poor solubility or the reactivity of the phosphonitrilic chloride. Chlorinated hydrocarbons, such as methylene chloride, are known to be very good solvents, but because of their toxicity they should not be used.

It has therefore been proposed that the hydrocarbons be substituted, for example by inorganic or organic acid halides (DE 42 21 854), by SiCl-containing compounds (DE 43 23 186, DE 43 23 188) or by cyclic siloxanes (DE 37 25 377). However, these variants have the disadvantage that the viscosity of the products rapidly rises as a result of hydrolysis and the subsequent condensation of the SiCl radicals under the action of moisture, and the products are then no longer able to be metered.

For specific applications of polysiloxanes or the products produced therefrom, too high a content of chlorine-containing compounds is unfavourable. In particular, very high purity is demanded of products which are used in medicine and medical technology and also in electrical engineering and electronics. In other fields too, the level of chlorine present in the products used is decisive owing to the formation of toxic materials in the case of fire.

Catalysts in which, starting from phosphonitrilic chloride, the chlorine content can be varied as desired and which are very suitable for the preparation of organosiloxanes or polyorganosiloxanes are not known.

DESCRIPTION OF THE INVENTION

It is an object of the invention to find a highly effective catalyst for the preparation of organosiloxanes and polyorganosiloxanes which are prepared primarily by condensation processes which catalyst has a chlorine content which can be set in a desired manner if required, dissolves homogeneously in the starting materials, is free of solvent and has a high stability with regard to viscosity and activity.

According to the invention, the catalyst is a reaction product of phosphonitrilic chloride with a compound of the general formula $$[R_3SiO(R_2SiO)_m]_3P{=}O \qquad (I),$$

where R are, independently of one another, identical or different, unsaturated and/or saturated monovalent hydrocarbon radicals having from 1 to 6 carbon atoms or hydrogen with the proviso that only one hydrogen atom is bound to each silicon atom and m has a value between 0 and 1000, with it being possible to completely or partially remove volatile chlorine-containing silicon compounds formed during the reaction.

The reaction of the phosphonitrilic chloride with the compound of the general formula $$[R_3SiO(R_2SiO)_m]_3P{=}O \quad (I),$$

can be carried out either at room temperature or at elevated temperature. However, siloxane cleavages can occur at higher temperatures.

The compound of the general formula $$[R_3SiO(R_2SiO)_m]_3P{=}O \quad (I)$$

which is used can, for example in the case of m=0 [tris (triorganosilyl) phosphate], be obtained by reaction of a triorganohalosilane, such as trimethylchlorosilane or dimethylvinylchlorosilane, with orthophosphoric acid in equivalent amounts, with water contained in the orthophosphoric acid being bound by the triorganohalosilane. To prepare the compound having m greater than 0, where m is able to take integral or fractional values [tris (triorganosiloxypolydiorganosiloxanyl) phosphate], the tris (triorganosilyl) phosphate obtained is reacted with one or more organocyclosiloxanes of the general formula $(R_2SiO)_q$ (II), where R are, independently of one another, identical or different, saturated and/or unsaturated monovalent hydrocarbon radicals having from 1 to 6 carbon atoms and q has values from 3 to 6.

The cyclic siloxanes required are, for example, prepared by alkaline depolymerization of products formed in the hydrolysis of diorganodichlorosilanes. They consist predominantly of octaorganocyclotetrasiloxane ($D_4$). Usually, the mixture obtained or a specific cyclosiloxane is used.

However, it is also possible to prepare the compound of the general formula (I) by any other known method.

Advantageously, the catalyst is prepared using a tris-(triorganosiloxypolydiorganosiloxanyl) phosphate of the general formula (I) having a ratio of trialkylsiloxy to dialkylsiloxy units corresponding to that of a polyorganosiloxane having trialkylsiloxy terminal groups at a viscosity of, for example, from 50 to 10,000 mPas, preferably of about 1000 mpas. In this way it is possible to set any desired catalytic activities independently of the viscosity of the catalyst.

The phosphonitrilic chloride used consists essentially of compounds or mixtures of these compounds of the general formula $[Cl_3PN(PCl_2N)_xPCl_3]^{+}*[P_yCl_{5y+1}]^{-}$, where x is an integer greater than/equal to 0 and y =0 or 1. It is obtained, for example, by reaction of 2 mol of phosphorus pentachloride with 1 mol of ammonium chloride as described in U.S. Pat. No. 3,839,388. Phosphonitrilic chloride is able to be reacted in any ratio with tris (triorganosiloxypolyorganosiloxanyl) phosphate of the general formula $[R_3SiO(R_2SiO)_m]_3P{=}O$ (I). It can be reacted as pure solid or as solution, e.g. dissolved in methylene chloride, but if a solution is used the solvent has to be removed after the reaction, for example together with the volatile chlorine-containing silicon compounds.

In the case of the removal of volatile chlorine-containing silicon compounds formed during the reaction, the compounds removed are mainly those of the general formula $ClSiR_2(OSiR_2)_xCl$ and/or of the general formula $ClSiR_3$, where R is as defined above and x has values between 1 and 20, for example trimethylchlorosilane. These compounds can be removed completely or partially from the reaction mixture. The removal is advantageously carried out by distillation at temperatures between 20° and 100° C., preferably between 40° and 80° C., and at atmospheric or reduced pressure, preferably at from 1 to 50 hPa.

Removal of the volatile chlorine-containing silicon compounds formed during the reaction makes it possible to reduce the chlorine content of the catalyst by any desired amount from 1 to 95% by weight, preferably by from 10 to 60% by weight, based on the amount of chlorine in the phosphonitrilic chloride used.

The catalyst of the invention can, prior to its use with organosiloxanes or polyorganosiloxanes which must not contain any condensable functional groups such as OH or alkoxy groups, be adjusted to the use concentration. These organosiloxanes can be starting materials or products of the condensation reaction. Cyclic or linear organosiloxanes having a viscosity of up to 1000 mPas are, for example, very suitable. It is thus possible to prepare a storage-stable catalyst concentrate which can be diluted to the desired concentration prior to use and does not have to be freshly prepared before each use. The concentrate has, like the more dilute solutions, excellent stability with regard to viscosity and activity.

The catalyst of the invention is outstandingly suitable for preparing organosiloxanes or polyorganosiloxanes by condensation and/or equilibration of one or more silicon compounds of the general formula $$R^1_a(R^2O)_bSiO_{(4-a-b)/2} \quad (III)$$

where $R^1$ are identical or different, saturated and/or unsaturated, substituted and/or unsubstituted monovalent hydrocarbon radicals having from 1 to 30 carbon atoms or hydrogen, with the proviso that only one hydrogen atom is bound to each silicon atom, $R^2$ is either hydrogen or $R^1$ and (a+b) has integral or fractional values greater than 1, with at least one oxygen per molecule being bound to the silicon. It is usually used in amounts of from 1 ppm by weight to 1% by weight, based on the weight of the amount of polyorganosiloxanes used in each case. Preference is given to using from 1 to 50 ppm by weight of catalyst, based on the amount of phosphonitrilic chloride which is used in the reaction with the compound of the general formula (I).

For example, polyorganosiloxanes having silanol groups can be reacted with one another or with polyorganosiloxanes having triorganosiloxy terminal groups in the presence of the catalyst of the invention. Polyorganosiloxanes having silanol groups which are used are here preferably α,ω-dihydroxypolydiorganosiloxanes of the general formula $HO(SiR_2O)_rH$ and polyorganosiloxanes having triorganosiloxy groups which are used are preferably α,ω-triorganosiloxypolydiorganosiloxanes of the general formula $R(R_2SiO)_sSiR_3$, where R are, independently of one another, identical or different, saturated and/or unsaturated monovalent hydrocarbon radicals having from 1 to 6 carbon atoms or hydrogen, with the proviso that only one hydrogen atom is bound to each silicon atom, and r and s have values greater than 2. Preference is given to using α,ω-dihydroxypolydimethylsiloxanes and α,ω-trimethylsiloxy-, α,ω-dimethylvinylsiloxy- or α,ω-dimethylhydrosiloxypolydimethylsiloxanes.

After the condensation and/or equilibration in the presence of the catalyst of the invention, the polyorganosiloxane obtained, which preferably has a viscosity in the range from $1 \cdot 10^{-1}$ to $10^5$ Pas, can be neutralized or stabilized. For this purpose, use can be made of basic or nucleophilic compounds such as, for example, compounds having epoxy groups, n-butyllithium or amines. Preferably, after reaching the target viscosity, the polyorganosiloxane obtained is admixed with an amine of the general formula $R'_nNH_{3-n}$, where R' are identical or different, saturated hydrocarbon radicals having from 1 to 10 carbon atoms and/or $R_3Si$ groups, where R are, independently of one another, identical or different, saturated or unsaturated hydrocarbons having from 1 to 6 carbon atoms and n has values between 1 and 3, preferably in amounts of from 1 ppm by weight to 1% by weight, based on the weight of the amount of polyorganosiloxane used. Preference is here given to using trialkylamine such as, for example, triisooctylamine, or hexaorganodisilazane such as, for example, hexamethyldisilazane or tetramethyldivinyldisilazane.

The catalyst of the invention can also be used for numerous further condensation reactions with participation of silanol groups and/or hydrolysable Si—X groups, such as, for example, alkoxy, acetoxy, amino, amido, aminoxy or epoxy groups. Typical reactions are, for example, the crosslinking of soluble mono- and/or diorganosiloxanes containing silanol and alkoxy groups to give insoluble silicone resins, the preparation of branched liquid siloxanes from α,ω-dihydroxypolydiorganosiloxanes and silanes and/or siloxanes having at least three hydrolysable groups, and also the acceleration of the condensation crosslinking of silicone rubber.

Besides the preparation of polymeric products, the catalysts of the invention can furthermore be used for preparing monomeric and oligomeric compounds. An example of this is the synthesis of defined, low-molecular-weight siloxanes from silanols and/or alkoxysilanes. The high activity of the catalysts of the invention compared with acid or basic catalysts is of particular advantage here.

The catalyst of the invention containing silicon, phosphorus, oxygen, nitrogen and, if desired, chlorine, is very suitable for preparing organosiloxanes and polyorganosiloxanes. It is solvent-free, clear and colourless, does not change its activity and viscosity even after a relatively long period of time and under the action of moisture and can be prepared with various viscosities and catalytic activities. A great advantage of the catalyst of the invention is that its chlorine content can be set to any desired value. Furthermore, it is soluble in any ratio in the polyorganosiloxanes used. The catalysts of the invention possess, even at significantly lower chlorine contents equal or higher activities in polycondensation reactions than pure phosphonitrilic chlorides which are used as solutions in methylene chloride.

EXAMPLES

A Preparation of Compounds of the General Formula (I)

A - 1 Preparation of tris(trimethylsilyl) phosphate

A 2.5 1 sulphonation flask equipped with dropping funnel, stirrer, thermometer and JUNGE distillation attachment with low-temperature condenser was charged with 2133 g of trimethylchlorosilane. Condenser cooling was carried out by means of refrigeration brine (−15° C.) with the aid of a cryostat. At the same time, the initially charged trimethylchlorosilane was heated to a gentle reflux. While stirring, 400 g of orthophosphoric acid (85% strength) were metered in via the dropping funnel at a rate of 100 ml/h ≈about 175 g/h. The escaping hydrogen chloride flowed through the condenser, in which entrained trimethyl-chlorosilane was largely condensed and flowed back to the reaction mixture, passed successively through the overpressure and underpressure safety devices and the bubble counter and was subsequently absorbed by the water present in two scrubbing bottles. After addition of the orthophosphoric acid, the reaction mixture was left for 12 hours under reflux, with stepwise increase of the liquid-phase temperature to about 110° C. After cooling, the volatiles removal from the reaction product was carried out in a subsequent vacuum distillation at 30 mbar up to a liquid-phase temperature of 60° C. The target product is obtained in the form of the distillation residue in an amount of 1.077 kg and was unambiguously identified as tris(trimethylsilyl) phosphate by $^{31}P$-NMR examination.

A - 2 Preparation of tris(dimethylvinylsilyl) phosphate

The procedure was similar to Example 1, except that 2369 g of dimethylvinylchlorosilane were used as triorganohalosilane. 1225 g of tris(dimethylvinylsilyl) phosphate were obtained.

A - 3 Preparation of tris (trimethylsiloxypolydimethylsiloxanyl) phosphate

For the reaction with the organocyclosiloxanes, 10 g of the tris(trimethylsilyl) phosphate were mixed with 90 g of polydimethylcyclosiloxanes containing from 3 to 6 siloxane units, and the mixture was left for 2 hours at 80° C. During this time, the viscosity of the product rose to about 30 mpas.

A - 4 Preparation of tris (dimethylvinylsiloxypolydimethylsiloxanyl) phosphate

The procedure was similar to Example 3, except that 10 g of tris(dimethylvinylsilyl) phosphate were used as tris (triorganosilyl) phosphate. After 2 hours at 80° C., the viscosity was about 30 mpas.

B Preparation of the Catalysts

All operations for preparing the catalyst were carried out using completely dry glass apparatus and with exclusion of atmospheric moisture (dry nitrogen atmosphere).

Phosphonitrilic Chloride

The phosphonitrilic chloride (PN) used as starting material was prepared as follows in accordance with U.S. Pat. No. 3,839,388: in a 1.5 1 sulphonation flask fitted with stirrer, Prahl attachment, thermometer, dropping funnel and low-temperature condenser, 99.1 g of 1,2,3-trichloropropane, 3.8 g of ammonium chloride and 32.8 g of phosphorus pentachloride were mixed with one another for 30 minutes at room temperature by means of intensive stirring. With uninterrupted stirring, the reaction mixture was heated first for 6 hours at 130° C. and then for a further 6 hours at 150° C. The 13.7 g of hydrogen chloride formed in the reaction were absorbed in a downstream scrubbing bottle filled with water. After the reaction is complete and the reaction mixture has been cooled to room temperature, the solvent was distilled off at a pressure of 5 mbar up to a liquid-phase temperature of 130° C. The 20 g of phosphonitrilic chloride obtained corresponded to the general formula $[Cl_3P{=}N(-PCl_2{=}N-)_xPCl_3]^{+}*[P_yCl_{5Y+1}]^{-}$, where x is an integer greater than/equal to 0 and y=0 or 1. For further reaction, it was possible to dilute as desired, for example with methylene chloride.

Catalyst "A"

25 ml (=36.05 g) of a 30% strength by volume phosphonitrilic chloride solution in methylene chloride were mixed with 15 g of tris(trimethylsilyl) phosphate and stirred for 3 hours at room temperature. Subsequently, 31.2 g of a mixture of trimethylchloro-silane and methylene chloride, containing 4.40 g of trimethylchlorosilane, were distilled off at a pressure of 600 mbar and a temperature of 40° C. 0.5 g of the bottom product, also described as concentrate, were mixed with 33.5 g of cyclic polydimethylsiloxanes. The reaction product obtained is a ready-to-use catalyst, with the concentration of the reacted phosphonitrilic chloride being 0.5% by weight.

Catalyst "B"

25 ml of a 30% strength by volume phosphonitrilic chloride solution in methylene chloride were mixed with 3.75 g of tris(trimethylsilyl) phosphate and stirred for 3 hours at room temperature. Subsequently, 28.4 g of a mixture of trimethylchlorosilane and methylene chloride, containing 2.29 g of trimethylchlorosilane, were distilled off at a pressure of 600 mbar and a temperature of 40° C. 0.5 g of the bottom product, also described as concentrate, are mixed with 65.5 g of cyclic polydimethylsiloxanes. The reaction product obtained is a ready-to-use catalyst, with the concentration of the reacted phosphonitrilic chloride being 0.5% by weight.

Catalyst "C"

10 ml (=14.4 g) of a 30% strength by volume phosphonitrilic chloride solution in methylene chloride were mixed with 15 g of tris(trimethylsilyl) phosphate and stirred for 3 hours at room temperature. Subsequently, 13.4 g of a mixture of trimethylchlorosilane and methylene chloride, containing 2.29 g of trimethylchlorosilane, were distilled off at a pressure of 600 mbar and a temperature of 40° C. 1.5 g of the bottom product, also described as concentrate, are mixed with 48.5 g of cyclic polydimethylsiloxanes. The reaction product obtained is a ready-to-use catalyst, with the concentration of the reacted phosphonitrilic chloride being 0.5% by weight.

Catalyst "D"

5.6 g of phosphonitrilic chloride were mixed with 2.24 g of tris(trimethylsilyl) phosphate and the mixture was stirred for 0.5 hours at a temperature of 60° C. Subsequently, 1.3 g of trimethylchlorosilane were distilled off at a pressure of 12 mbar and a temperature of 60° C. The bottom product, also described as concentrate, was mixed with 1113.5 g of a mixture of cyclic polydimethylsiloxanes containing octamethylcyclotetrasiloxane as main component. The reaction product obtained is a ready-to-use catalyst, with the concentration of the reacted phosphonitrilic chloride being 0.5% by weight.

Catalyst "E"

2.5 g of phosphonitrilic chloride were mixed with 17.6 g of tris(trimethylsilyl) phosphate and the mixture was stirred for 0.5 hours at a temperature of 60° C. Subsequently, 3.57 g of trimethylchlorosilane were distilled off at a pressure of 12 mbar and a temperature of 60° C. The bottom product, also described as concentrate, was mixed with 483.5 g of a mixture of cyclic polydimethylsiloxanes containing octamethylcyclotetrasiloxane as main component. The reaction product obtained is a ready-to-use catalyst, with the concentration of the reacted phosphonitrilic chloride being 0.5% by weight.

Catalyst "F"

5.6 g of phosphonitrilic chloride were mixed with 3.53 g of tris(trimethylsilyl) phosphate and the mixture was stirred for 0.5 hours at a temperature of 60° C. The reaction product, also described as concentrate, was mixed with 1110.9 g of a mixture of cyclic polydimethylsiloxanes containing octamethylcyclotetra-siloxane as main component. The reaction product obtained is a ready-to-use catalyst, with the concentration of the reacted phosphonitrilic chloride being 0.5% by weight.

Catalyst "X" (comparative catalyst)

0.5% strength by volume solution of phosphonitrilic chloride in methylene chloride.

C Use of the Catalysts

The trials described below are to illustrate the properties of the catalysts prepared. All viscosities are based on 25° C.

I. Continuous preparation of linear polyorganosiloxanes (preferred embodiment)

Example 1

A laboratory thin-film evaporator having an evaporation surface of 0.06 $m^2$ was continuously supplied with 1.98 kg/h of α,ω-dihydroxypolydimethylsiloxane having a viscosity of 160 mPas and also with 0.7932 ml/h of the catalysts prepared as described in Examples "A" to "X". The temperature on the evaporator surface was 140° C., the pressure was 80 mbar and the rotor speed was set to 400 rpm. The polymer was continuously stabilized with 0.8 g/min of a 0.025% strength by weight solution of triisooctylamine in α,ω-dihydroxypolydimethylsiloxane having a viscosity of 160 mPas. The viscosity of the polymer was measured using a process viscometer and converted to a temperature of 25° C. The viscosity measured with adherence to these conditions can be regarded as a measure of the reaction rate and accordingly also indicates the relative activity of the catalyst used. The properties of the catalysts "A" to "X" and the results achieved therewith are summarized in Table 1.

TABLE 1

| Catalyst | Ratio PN:silyl phosphate | Original Cl content[1]) [% by weight] | Cl content after Cl removal [% by weight] | Relative lowering of Cl content [%] | Viscosity obtained [Pas] |
|---|---|---|---|---|---|
| A | 0.5 | 0.37 | 0.276 | 25.3 | 20 |
| B | 2 | 0.38 | 0.330 | 13.2 | 25 |
| C | 0.2 | 0.38 | 0.255 | 32.9 | 21 |
| D | 2.5 | 0.36 | 0.324 | 10.0 | 25 |
| E | 0.14 | 0.37 | 0.143 | 61.4 | 20 |
| F | 0.63 | 0.37 | 0.37 | 0 | 20 |
| X | — | 0.38 | 0.38 | 0 | 10–21[2]) |

[1])Converted to ready-to-use catalyst containing 0.5% by weight of reacted phosphonitrilic chloride

[2])Great variations due to instability of the reaction because of inhomogeneous distribution of the catalyst Example 2

A laboratory thin-film evaporator having an evaporation surface of 0.06 $m^2$ was supplied continuously with 2.12 kg/h of a mixture of 90% by weight of a α,ω-dihydroxypolydimethylsiloxane having a viscosity of 160 mpas and 7% by weight of a α,ω-trimethylsiloxypolydimethylsiloxane having a viscosity of 50 mPas and also with 4.24 ml/h of the catalysts prepared as described in Examples "A" to "X". The temperature on the evaporator surface was 120° C., the pressure was 1 mbar and the rotor speed was set to 200 rpm. The polymer was continuously stabilized with 1.4 g/min of a 0.25% strength by weight solution of triisooctylamine in a α,ω-trimethylsiloxypolydimethylsiloxane having a viscosity of 50 mpas. The viscosity of the polymer was measured using a process viscometer and converted to a temperature of 25° C. The minimization of the content of silicon-bonded OH groups which was measured with adherence to these conditions can be regarded as a measure of the reaction rate and accordingly also indicates the relative activity of the catalyst used.

The results achieved using the catalysts "A" to "X" in condensation reactions for preparing linear polyorganosiloxanes having a target viscosity of 10,000 mPas are summarized in Table 2.

TABLE 2

| Catalyst | Viscosity [mPas] | Content of silicon-bonded OH groups [ppm] |
|---|---|---|
| A | 11200 | 25 |
| B | 9900 | 15 |
| C | 10500 | 25 |
| D | 9850 | 10 |

TABLE 2-continued

| Catalyst | Viscosity [mPas] | Content of silicon-bonded OH groups [ppm] |
|---|---|---|
| E | 10250 | 20 |
| F | 10350 | 30 |
| X | 11720 | 45 |

As can be seen from Table 2, the silanol content of the linear polyorganosiloxanes prepared using the catalysts of the invention "A" to "G" is lower than when the catalyst "X", which is not according to the invention, is used. This demonstrates the higher activity of the catalysts of the invention.

II. Batchwise preparation of Linear Polyorganosiloxanes

Example 3

In a 350 ml sulphonation flask fitted with dissolver stirrer, internal thermometer and distillation attachment, 150 g of a α,ω-dihydroxypolydimethylsiloxane having a viscosity of 160 mPas at 25° C. were heated to 100° C. while stirring. After addition of 300 μl of the catalyst "F", the pressure in the reaction vessel was lowered to 100 mbar. After 5 minutes, measured from the time of catalyst addition, air was admitted to the reaction vessel. 4.5 μl of triisooctylamine were mixed in over a further period of 5 minutes. The α,ω-dihydroxypolydimethylsiloxane obtained had a viscosity of 293 Pas at 25° C.

Example 4

In a 350 ml sulphonation flask fitted with dissolver stirrer, internal thermometer and distillation attachment, 150 g of a mixture of 96.5% by weight of α,ω-dihydroxypolydimethylsiloxane having a viscosity of 160 mPas at 25° C. and 3.5% by weight of α,ω-bis(trimethylsiloxy)polydimethylsiloxane containing 4.76% by weight of trimethylsiloxy units were heated to 100° C. while stirring. After addition of 0.6 ml of the catalyst "F", the pressure in the reaction vessel was lowered to 20 mbar. After 30 minutes, measured from the time of catalyst addition, air was admitted to the reaction vessel. 5.4 μl of hexamethyldisilazane were then mixed in.

The α,ω-bis(trimethylsiloxy)polydimethylsiloxane obtained had a viscosity of 16,700 mPas at 25° C. and a silicon-bonded hydroxyl group content, determined by IR spectroscopy, of <30 ppm.

III. Continuous Preparation of High-Molecular-Weight Polyorganosiloxanes

Catalyst "H"

20 ml of a 10% strength by volume phosphonitrilic chloride solution in methylene chloride were mixed with 8 g of the reaction product of one part of tris(trimethylsilyl) phosphate and nine parts of the mixture of cyclic compounds from Example 1. After the mixture had stood for about 3 hours at room temperature, a further 90 g of the mixture of cyclic compounds of the known composition were added. After standing further for about 2 hours, a colourless and completely clear solution was obtained. The methylene chloride was removed by vacuum distillation at ≦10 mbar and a maximum of 50° C. The product obtained had a viscosity of about 1000 mpas at 25° C., the concentration of the reacted phosphonitrilic chloride was 2% by weight.

Example 5

In a heated twin-screw vacuum compounder, the following were mixed and heated to 100° C.: 8.0 kg of α,ω-dihydroxypolydimethylsiloxane having a viscosity of 160 mPas at 25° C., 0.02 kg of α,ω-bis(dimethylvinylsiloxy) dimethylsiloxane containing 10% by weight of dimethylvinylsiloxy units and 0.12 kg of α,ω-dihydroxypolymethylvinylsiloxane having a viscosity of 9500 mPas at 25° C. and containing 4.7% by weight of silicon-bonded vinyl groups. After addition of 8 g of the catalyst "H", the pressure in the compounder was lowered to 9 mbar. After a reaction time of 2 hours, nitrogen was admitted and subsequently 8 g of tetramethyldivinyldisilazane were mixed in. After a further 2 hours, the pressure in the reaction space was lowered to 4 mbar and the mixture was compounded for one hour at 120° C. The α,ω-bis(dimethylvinylsiloxy)polydimethylsiloxymethylvinylsiloxane obtained had a viscosity of 56,000 Pas at 25° C. To confirm the very substantial absence of silicon-bonded hydroxyl groups, 3 g of a mixture of 20% by weight of dibutyltin laurate and 80% by weight of tetraethoxysilane were worked into 60 g of the polysiloxane obtained in the manner described, using a plastograph at a test temperature of 20±1° C. over a period of one hour. No increase in viscosity was observed.

IV. Preparation of Branched Polyorganosiloxanes

Example 6

400 parts by weight of an α,ω-dihydroxypolydimethylsiloxane having a viscosity of 70 mpas, 40 parts by weight of an α,ω-trimethylsiloxypolydimethylsiloxane having a viscosity of 40 mPas, 4 parts by weight of methyltrimethoxysilane and one part by weight of catalyst "D" were heated to 100° C. Over the course of 20 minutes, the pressure was lowered to 35 mbar. The catalyst was then neutralized using 0.015 part by weight of triisooctylamine. The polysiloxane obtained had a viscosity of 19,000 mpas.

Example 7

A mixture of 80 parts by weight of an α,ω-dihydroxypolydimethylsiloxane having a viscosity of 50,000 mpas, 160 parts by weight of an α,ω-trimethylsiloxypolydimethylsiloxane having a viscosity of 1000 mPas and 4.5 parts by weight of a pyrogenic, hydrophilic silica having a surface area of 150 $m^2/g$ were heated to 115° C. for 30 minutes in the presence of one part by weight of catalyst "D". After neutralization using 0.015 part by weight of triisooctylamine, a polyorganosiloxane having a viscosity of 6800 mpas was obtained.

Example 8

A mixture of 80 parts by weight of an α,ω-dihydroxypolydimethylsiloxane having a viscosity of 50,000 mpas, 160 parts by weight of an α,ω-trimethylsiloxypolydimethylsiloxane having a viscosity of 1000 mPas and 7.7 parts by weight of a 60% strength toluene solution of a methylsilicone resin comprising $(CH_3)_3SiO_{1/2}$ and $SiO_{4/2}$ units in a ratio of 0.8:1 were heated to 115° C. for 30 minutes in the presence of one part by weight of catalyst "D". After neutralization using 0.015 part by weight of triisooctylamine, a polyorganosiloxane having a viscosity of 2550 mPas was obtained.

Example 9

A mixture of 27 parts by weight of an α,ω-dihydroxypolydimethylsiloxane having a viscosity of 12,500 mPas, 57 parts by weight of an α,ω- trimethylsiloxypolydimethylsiloxane having a viscosity of 1000 mPas and 5.4 parts by weight of an ethyl polysilicate containing 40% by weight of $SiO_2$ were heated to 115° C. for 30 minutes in the presence of one part by weight of catalyst "D". After neutralization using 0.015 part by weight of triisooctylamine, a polyorganosiloxane having a viscosity of 5300 mPas was obtained.

Use of the Branched Polyorganosiloxanes

5% by weight of hydrophobic silica having a BET surface area of 90 $m^2/g$ were mixed into 190 g of the polyorganosiloxanes obtained from Examples 3 to 6 for 30 minutes by means of a dissolver disc at 1900 rpm and their action as antifoaming agents was assessed. Both in the presence of strongly foaming anionic surfactants and in the presence of high concentrations of nonionic surfactants, the polyorganosiloxanes prepared using the catalyst of the invention had excellent effectiveness as antifoaming agents, even for low added amounts.

We claim:

1. A catalyst obtained by reaction of phosphonitrilic chloride with a compound of the general formula $$[R_3SiO(R_2SiO)_m]_3P{=}O \quad (I),$$

where R are, independently of one another, identical or different, unsaturated and/or saturated monovalent hydrocarbon radicals having from 1 to 6 carbon atoms or hydrogen, with the proviso that only one hydrogen atom is bound to each silicon atom and m has a value between 0 and 1000.

2. Catalyst according to claim 1, wherein volatile chlorine-containing silicon compounds formed during the reaction are completely or partially removed.

3. Catalyst according to claim 2, wherein the volatile chlorine-containing silicon compounds formed during the reaction are completely removed.

4. Catalyst according to claim 2, wherein the chlorine content is reduced by from 1 to 95% by weight, based on the amount of chlorine in the phosphonitrilic chloride.

5. Catalyst according to claim 4, wherein the chlorine content is reduced by from 10 to 60% by weight, based on the amount of chlorine in the phosphonitrilic chloride.

6. A concentrate comprising the catalyst according to claim 1 and one or more organosiloxanes or polyorganosiloxanes not containing any condensable functional groups.

7. Process for preparing the compound of the general formula $$[R_3SiO(R_2SiO)_m]_3P{=}O \quad (I)$$

where m =0, and R are, independently of one another, identical or different, unsaturated and/or saturated monovalent hydrocarbon radicals having from 1 to 6 carbon atoms or hydrogen, with the proviso that only one hydrogen atom is bound to each silicon atom, comprising reacting molar equivalent amounts of triorganohalosilane and orthophosphoric acid and reacting molar equivalent amounts of said triorganohalosilane and water present with said orthophosphoric acid.

8. Process according to claim 7, wherein the triorganohalosilane is trimethylchlorosilane.

9. Process according to claim 7, wherein the triorganosilane is dimethylvinylchlorosilane.

10. A method of preparing organosiloxanes or polyorganosiloxanes, comprising condensing or equilibrating one or more silicon compounds of the formula $$R^1_a(R^2O)_bSiO_{(4-a-b)/2} \quad (III),$$

where each $R^1$ is an identical or different, saturated or unsaturated, substituted or unsubstituted monovalent hydrocarbon radical having from 1 to 30 carbon atoms or hydrogen in the presence of the catalyst of claim 1, with the proviso that only one hydrogen atom is bound to each silicon atom, $R^2$ is either hydrogen or $R^1$ and (a+b) has integral or fractional values greater than 1, with at least one oxygen per molecule being bound to silicon.

11. The method according to claim 10, wherein the catalyst is present in amounts of from 1 ppm by weight to 1% by weight, based on the weight of said silicon compounds.

12. The method according to claim 11, wherein the catalyst is used in amounts from 1 ppm by weight to 50 ppm by weight, based on the weight of said silicon compounds.

13. Process for preparing the compound of general formula $$[R_3SiO(R_3SiO)_m]P{=}O \quad (I)$$

where m is from 3 to 1000, and R are, independently of one another, identical or different, unsaturated and/or saturated monovalent hydrocarbon radicals having from 1 to 6 carbon atoms or hydrogen, with the proviso that only one hydrogen atom is bound to each silicon atom, comprising reacting a tris(triorganosiloxypolyorganosiloxanyl) phosphate of the general formula $(R_3SiO)_3P{=}O$ with one or more organocyclosiloxanes of the general formula $$(R_2SiO)_q \quad (II),$$

where q is from 3 to 12, in a molar ratio of from 1:1 to 500:1.

* * * * *